US008244015B2

(12) United States Patent
Sirohey et al.

(10) Patent No.: US 8,244,015 B2
(45) Date of Patent: Aug. 14, 2012

(54) METHODS AND APPARATUS FOR DETECTING ANEURYSM IN VASCULATURES

(75) Inventors: Saad Ahmed Sirohey, Pewaukee, WI (US); Gopal B. Avinash, New Berlin, WI (US); Tamanna N. Bembenek, Milwaukee, WI (US); Jérôme Francois Knoplioch, Neuilly sur Seine (FR)

(73) Assignee: General Electric Company, Schenectady, NY (US)

( * ) Notice: Subject to any disclaimer, the term of this patent is extended or adjusted under 35 U.S.C. 154(b) by 1083 days.

(21) Appl. No.: 11/603,717

(22) Filed: Nov. 22, 2006

(65) Prior Publication Data

US 2008/0118127 A1    May 22, 2008

(51) Int. Cl.
*G06K 9/00* (2006.01)
(52) U.S. Cl. ...................................... 382/130
(58) Field of Classification Search ........... 382/100, 382/128, 129, 130, 131, 132, 133, 134, 173, 382/181; 378/1, 37, 21, 41, 42, 38, 44, 51, 378/62, 65, 146; 128/920; 600/300, 407
See application file for complete search history.

(56) References Cited

U.S. PATENT DOCUMENTS

| | | | |
|---|---|---|---|
| 4,577,152 A | 3/1986 | Macovski | |
| 5,128,864 A | 7/1992 | Waggener | |
| 5,307,264 A | 4/1994 | Waggener | |
| 5,430,783 A | 7/1995 | Hu et al. | |
| 5,647,018 A | 7/1997 | Benjamin | |
| 5,673,300 A | 9/1997 | Reckwerdt et al. | |
| 5,694,530 A | 12/1997 | Goto | |
| 5,720,291 A | 2/1998 | Schwartz | |
| 5,740,222 A | 4/1998 | Fujita et al. | |
| 5,900,878 A | 5/1999 | Goto et al. | |
| 5,920,660 A | 7/1999 | Goto | |
| 6,011,862 A * | 1/2000 | Doi et al. ................ 382/132 |
| 6,331,116 B1 | 12/2001 | Kaufman et al. | |
| 6,477,401 B1 | 11/2002 | Johnson et al. | |
| 6,603,494 B1 | 8/2003 | Banks et al. | |
| 6,925,200 B2 | 8/2005 | Wood et al. | |
| 6,947,784 B2 | 9/2005 | Zalis | |
| 6,990,231 B2 | 1/2006 | Goto | |
| 7,027,630 B2 | 4/2006 | Bruijns | |
| 7,072,501 B2 | 7/2006 | Wood et al. | |

(Continued)

FOREIGN PATENT DOCUMENTS

JP        08267292 A    10/1996
(Continued)

OTHER PUBLICATIONS

Subasic et al., "3-D image analysis of abdominal aortic aneurysm" Medical Imaging 2001: Image Processing, Proceedings of SPIE vol. 4322(2001), p. 388-394.*

(Continued)

*Primary Examiner* — Bhavesh Mehta
*Assistant Examiner* — Tahmina Ansari
(74) *Attorney, Agent, or Firm* — The Small Patent Law Group; Dean D. Small (57) ABSTRACT

Methods and apparatus for detecting aneurysm in vasculatures are provided. The method includes removing bone structures from three-dimensional (3D) computed tomography (CT) angiography image data and extracting spherical shapes from the bone removed 3D CT angiography image data. The method further includes displaying the extracted spherical shapes on an image of the 3D CT angiography image data.

21 Claims, 5 Drawing Sheets

U.S. PATENT DOCUMENTS

| | | | |
|---|---|---|---|
| 7,123,760 | B2 | 10/2006 | Mullick et al. |
| 2004/0066958 | A1* | 4/2004 | Chen et al. ............... 382/128 |
| 2004/0101183 | A1* | 5/2004 | Mullick et al. ............ 382/131 |
| 2004/0249270 | A1* | 12/2004 | Kondo et al. ............... 600/425 |
| 2005/0094858 | A1 | 5/2005 | Sirohey et al. |
| 2005/0147297 | A1 | 7/2005 | McLaughlin et al. |
| 2005/0259854 | A1 | 11/2005 | Arimura et al. |
| 2006/0074285 | A1 | 4/2006 | Zarkh et al. |
| 2006/0079743 | A1* | 4/2006 | Ferrant et al. ............. 600/407 |
| 2006/0079761 | A1 | 4/2006 | Tu et al. |
| 2006/0094961 | A1 | 5/2006 | Mikheev et al. |
| 2006/0215896 | A1 | 9/2006 | Sirohey et al. |
| 2006/0241427 | A1* | 10/2006 | Kinouchi et al. .......... 600/437 |
| 2007/0019846 | A1* | 1/2007 | Bullitt et al. ............... 382/128 |
| 2007/0019850 | A1 | 1/2007 | Knoplioch et al. |
| 2007/0127803 | A1 | 6/2007 | Yoshida et al. |
| 2007/0127804 | A1 | 6/2007 | Yoshida et al. |
| 2007/0133878 | A1* | 6/2007 | Porikli et al. .............. 382/190 |
| 2007/0165928 | A1 | 7/2007 | Yoshida et al. |
| 2009/0279752 | A1* | 11/2009 | Sirohey et al. ............. 382/128 |

FOREIGN PATENT DOCUMENTS

| | | |
|---|---|---|
| JP | 09156689 A | 6/1997 |
| WO | WO-03/0452222 A2 | 6/2003 |
| WO | WO 2005/023086 A2 | 3/2005 |

OTHER PUBLICATIONS

Lell et al., "Clinical evaluation of bone-subtraction CT angiography in head and neck imaging", European Radiology, vol. 16, No. 4, 889-897, DOI: 10.1007/s0330-005-0032-1, Published Nov. 2005.*

Tomandl et al., "Bone-Subtraction CT Angiography for the Evaluation of Intracranial Aneurysms" American Journal of Neuroradiology, AJNR Jan. 2006 27: 55-59.*

Sonka and J Michael Fitzpatrick et al., Handbook of Medical Imaging, vol. 2, Medical Image Processing and Analysis, Jan. 1, 2000, pp. 711-810, 898-914.

Saad Sirohey; "Lung VCAR"; General Electric company; 6 pages, GE 2005.

Lichan Hong; "Virtual Voyage: Interactive Navigation in the Human Colon"; Center for Visual Computing State University of New York at Stony Brook; 8 pages, SIGGRAPH Conference, 1997.

Laurent Saroul, et al.; "Distance Preserving Flattening of Surface Sections", IEEE Transactions on Visualization and Computer Graphics, vol. 12, No. 1, Jan.-Feb. 2006, 10 pgs.

Foreign Search Report, Netherlands Application No. 1034671, Dated Oct. 20, 2008 (15 pages).

Hirai et al., Intracranial Aneurysms at MR Angiography: Effect of Computer-aided diag on Radiologists Det. Perf., Radiology 2005; 237:605-610, RSNA 2005.

Doi, Current status and future potential of computer-aided diagnosis in medical imaging, British Journal of Radiology (2005) 78, S3-s19.

Kobashi et al., Computer-aided diagnosis of intracranial aneurysms in MRA images with case-based reasoning, IEICE Transactions on Information and Systems 2006 E89-D(1):340-350.

Uchiyama et al., Computer-aided diagnosis scheme for detection of unruptured intracranial aneurysms in MR angiography, Eng in Med and Bio Society, 2005; IEEE-EMBS 20.

Nicholas Ayache (ED.); Visualization of Multimodal Images for Neurosurgical Planning and Guidance, Lecture Notes in Computer Science, "Computer Vision, Virtual Reality and Robotics in Medicine", First International Conference, CVRMed '95, Nice, France, Apr. 1995 Proceedings; 10 pages.

Frederik Maes et al; Lecture Notes in Computer Science, "Computer-Aided Interactive Object Delineation Using an Intelligent Paintbrush Technique"; First International Conference, CVRMed '95, Nice, France, Apr. 1995 Proceedings pp. 77-83.

Jed Lengyel et al.; Lecture Notes in Computer Science, "Three-Dimensional Reconstructions and Volume Rendering of Intravascular Ultrasound slices Imaged on a Curved Arterial Path"; First International Conference, CVRMed '95, Nice, France, Apr. 1995 Proceedings pp. 399-405.

Robert A. Drebin et al.; "Volume Rendering"; Computer Graphics, vol. 22, No. 4, Aug. 1988; pp. 65-74.

Karel J Zuiderveld et al.; "Multi-Modal Volume Visualization Using Object-Oriented Methods"; 0-8186-7067-3/95, 1995 IEEE pp. 59-66 and 129.

Max A Viergever; "Integrated Presentation of Multimodal Brain Images", Brain Topography, vol. 5, No. 2, 1992; pp. 135-145.

Markus Hardwiger et al.; "High-Quality Two-Level Volume Rendering of Segmented Data Sets on Consumer Graphics Hardware"; 8 pgs, 2003 Proc 14th IEEE Visualization Conf.

Jean-Jose Jacq et al; "A Direct Multi-Volume Rendering Method. Application to Visual Assessment of 3-D Image Registration Algorithms"; 10 pgs, VBC 1996 Proc 4th Int'l Conf on Visualization Biomedical Computing.

Paul J Keller, Phd, et al.; "MR Angiography with Two-dimensional Acquisition and Three-Dimensional Display"; Radiology, Nov. 1989, pp. 527-532.

Philippe G. Lacroute; "Fast Volume Rendering Using a Shear-Warp Factorization of the Viewing Transformation"; Technical Report: CSL-TR-95-678; Stanford Center for Integrated Systems, ARPA/ONR Contracts N00039-91-C-0138, 175-6212-1, NSF Contract CCR-9157767; 236 pages, Sep. 1995.

Pascal Volino et al.; Efficient Self-collision Detection on Smoothly Discretized Surface Animations using Geometrical Shape Regularity; MIRALab Copyright © Information 1998; MIRALab, University of Geneva; 18 pages.

Cai et al., Special session on colon liver and Brain CAD, Int J CARS (2006) 1:369-388.

Hisanori et al., Development of cerebral aneurysm computer-aided detection systems with 3D mra data, Yokogawa Technical Report English Edition, No. 39 (2005).

Ninomiya et al., Feature Extraction from MRA Images for Fuzzy Rule-based Diagnosis of Cerebral Aneurysms, http://scholar.google.com/scholar?hl=en&lr=&q=cache:zcJ5_ZuD34oJ:wwwj3.comp.eng.himeji-tech.as.jp/staff/kobashi/reprints/SCIS2002-ninomiya.pdf, Date: 2003.

Ando et al., Computer-aided diagnosis scheme for detection of unruptured intracranial aneurysms in MR angiography, Eng in Med and Bio Society, 2005; IEEE-EMBS 20.

Nicholas Ayache, Computer Vision, Virtual Reality and Robotics in Medicine, First International Conference, CVRMed '95, Nice, France, Apr. 1995 Proceedings, (10) pgs.

Frederik Maes, et al., Computer-Aided Interactive Object Delineation Using an Intelligent Paintbrush Technique, Lecture Notes in Computer Science, First International Conference, CVRMed '95, Nice, France, Apr. 1995 Proceedings, pp. 77-83.

Jed Lengyel, et al., Lecture Notes in Computer Science, Three-Dimensional Reconstruction and Volume Rendering of Intravascular Ultrasound Slices Imagedon a Curved Arterial Path, First International Conference, CVRMed '95, Nice, France, Apr. 1995 Proceedings, pp. 399-405.

Robert A. Drebin, et al., Volume Rendering, Computer Graphics, vol. 22, No. 4, Aug. 1988, (10) pgs.

Zuiderveld, et al., Multi-Modal Volume Visualization Using Object-Oriented Methods, 1995, IEEE, pp. 59-66 and 129.

Viergever, et al., Integrated Presentation of Multimodal Brain Images, Brain Topography, vol. 5, No. 2, 1992, pp. 135-145.

Markus Hadwiger, et al., High-Quality Two-Level Volume Rendering of Segmented Data Sets on Consumer Graphics Hardware, VRVis Research Center Austria, (8) pages, 2003 Proc 14th IEEE Visualization Conf.

Jean-Jose Jacq, et al., A Direct Multi-Volume Rendering Method. Application to Visual Assessment of 3-D Image Registration Algorithms, Department image et Traitement de l'Information, Telecom Bretagne, B.P. 832-29285 Brest Cedex—France, (10) pages, 1996 VBC 4thProc Int Conf.

Paul J. Keller, et al., MR Angiography With Two-Dimensional Acquisition and Three-Dimensional Display, Radiology 1989; 173: 527-532.

Philippe G. Lacroute, Fast Volume Rendering Using a Shear-Warp Factorization of the Viewing Transformation, Technical Report:

CSL-TR-95-678; Stanford Center for integrated Systems, ARPA/ONR Contracts N00039-91-C-0138, 175-6212-1, NCFContract CCR-9157767; 236 pgs, Sep. 95.

Pascal Volino, et al., Efficient Self-Collision Detection on Smoothly Discretized Surface Animations Using Geometrical Shape Regularity, MIRALab Copyright Information 1998; MIRLab, University of Geneva, (18) pgs.

Tracy L. Faber, et al., Three-Dimensional Fusion of Coronary Arteries With Myocardial Perfusion Distributions: Clinical Validation, The Journal of Nuclear Medicine, vol. 45, No. 5, May 2004, pp. 745-753.

Zigang Wang, et al., An Improved Electronic Colon Cleansing Method for Detection of Polyps by Virtual Colonoscopy, Proceedings of the 2005 IEEE Engineering in Medicine and Biology 27th Annual Conference. Shanghai, China, Sep. 1-4, 2005, pp. 6512-6515.

Franaszek, et al , Hybrid Segmentation of Colon Filled With Air and Opacified Fluid for CT Colonoscopy, IEEE Transactions on Medical Imaging. vol. 25, No. 3, Mar. 2006, pp. 358-368.

Zigang Wang, et al., An Improved Electronic Colon Cleansing Method for Detection of Polyps by Virtual Colonoscopy, IEEE Transactions on Biomedical Engineering. vol. 53. No. 8, Aug. 2006. pp. 1635-1646.

* cited by examiner

METHODS AND APPARATUS FOR DETECTING ANEURYSM IN VASCULATURES

BACKGROUND OF THE INVENTION

This invention relates generally to imaging, and more particularly, to detecting aneurysm in vasculature, especially in the brain, using a shape based method.

Aneurysms are a fundamental cause of hemorrhagic stroke and account for about twenty percent of all stroke cases. In an aneurysm, a portion of the brain ruptures and is filled with blood that can cause tissue death or pressure in the head. Large hemorrhages can be fatal and can be caused by large aneurysms that are typically clearly visible on a medical image. However, of particular interest and concern is the debilitating "dementia" like conditions caused by micro hemorrhages that are due to small aneurysm ruptures.

Aneurysms are infrequently encountered on a straight, non-branching segment of an intracranial artery. However, the aneurysms occurring on straight, non-branching segments are more often found to have sacs that point longitudinally along the wall of the artery in the direction of blood flow and to project only minimally above the adventitial surface. Aneurysms having these characteristics are of a dissecting type rather than of the congenital saccular type. The development of these aneurysms is caused more frequently by the onset of ischemic neurological deficits than by the subarachnoid hemorrhage associated with congenital saccular aneurysms.

The problem of detecting small aneurysms is particularly difficult for computed tomography angiography (CTA) exams as these aneurysms are very minute and are often indistinguishable from the vasculature. Additionally, the presence of bone in the skull causes added difficulty to visualize these structures. Thus, these aneurysms in the vascular network may not be detected by a typical CTA exam.

Known visualization methods provide complementary shape information that can aid in diagnosis of anatomical and/or clinical conditions. However, these template based methods provide information that can tend to overwhelm the user with either fragmented or at times false clinical information. Thus, even when this information is accurate, it is not presented to the user in a clinically efficient manner. The problem with inaccurate information is further compounded in CTA exams where the presence of bones can introduce filtering artifacts due to the shape similarities with objects of interest. This can lead to improper or incorrect diagnosis.

BRIEF DESCRIPTION OF THE INVENTION

In one embodiment, a method for detecting aneurysms is provided. The method includes removing bone structures from three-dimensional (3D) computed tomography (CT) angiography image data and extracting spherical shapes from the bone removed 3D CT angiography image data. The method further includes displaying the extracted spherical shapes on an image of the 3D CT angiography image data.

In another embodiment, a method for detecting abnormalities is provided. The method includes removing bone structures from three-dimensional (3D) computed tomography (CT) angiography image data and extracting at least one of shape based features and texture based features from the bone removed 3D CT angiography image data. The method further includes identifying abnormalities based on the extracted features.

In yet another embodiment, a medical imaging apparatus having a radiation source, a detector array, an image processor, a display, and a memory is provided. The medical imaging apparatus is controlled by a computer configured to operate the medical imaging apparatus to produce angiographic medical images using the radiation source, the detector array, the image processor, the display, and the memory. The memory has stored therein instructions configured to instruct the computer to generate an image having extracted shapes displayed thereon. The instructions comprise instructions configured to instruct the computer to remove bone structures from three-dimensional (3D) computed tomography (CT) angiography image data, extract spherical shapes from the bone removed 3D CT angiography image data, and display the extracted spherical shapes on an image of the 3D CT angiography image data.

In still another embodiment, a machine-readable medium or media is provided having instructions recorded thereon configured to instruct a computer to generate an image having extracted shapes displayed thereon. The instructions comprise instructions configured to instruct the computer to remove bone structures from three-dimensional (3D) computed tomography (CT) angiography image data, extract spherical shapes from the bone removed 3D CT angiography image data and display the extracted spherical shapes on an image of the 3D CT angiography image data.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments of the present invention in which data representing an image is generated but a viewable image is not. However, many embodiments generate (or are configured to generate) at least one viewable image.

Embodiments of the present invention provide a shape based method of aneurysm detection in a computed tomography angiography (CTA) exam. Technical effects of the present invention include, but are not limited to processing image data to extract spherical shapes useful in detecting aneurysms in images formed form the image data. It should be noted that as used herein, unless referring to an image actually being displayed, the scope of the subject matter referred to by the term "image" is also intended to include data representing an image, for example, an image in a form useful for processing by a computer.

Figure 1:
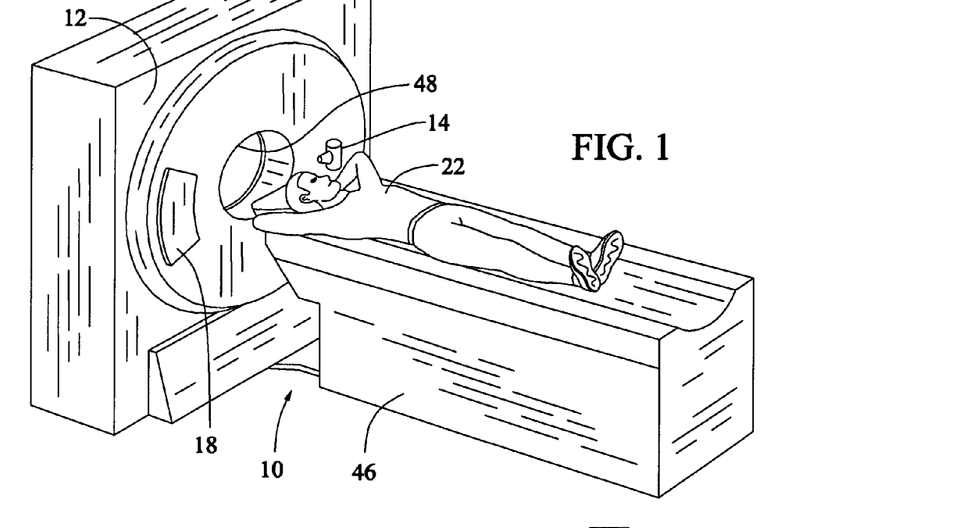
FIG. 1 is a pictorial drawing of an embodiment of a computed tomography (CT) imaging system of the present invention.
Figure 2:
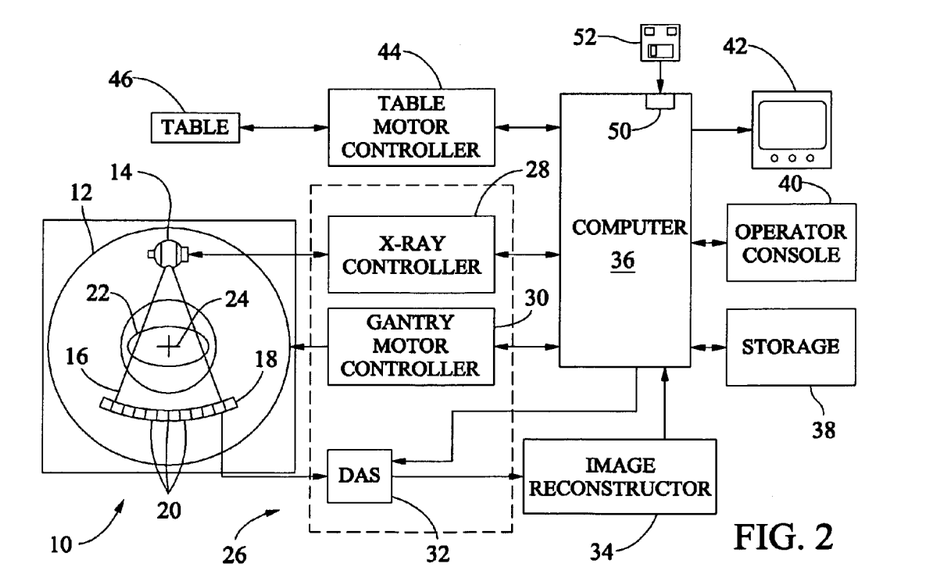
FIG. 2 is a schematic block diagram of the CT imaging system of FIG. 1.

Referring to FIGS. 1 and 2, a multi-slice scanning imaging system, for example, a Computed Tomography (CT) imaging system 10 is shown as including a gantry 12, such as representative of a "third generation" CT imaging system. The gantry 12 has an x-ray tube 14 (also called x-ray source 14 herein) that projects a beam of x-rays 16 toward a detector array 18 on the opposite side of the gantry 12. The detector array 18 is formed by a plurality of detector rows (not shown) including a plurality of detector elements 20 that together sense the projected x-rays that pass through an object, such as a medical patient 22 between the array 18 and the source 14. Each detector element 20 produces an electrical signal that represents the intensity of an impinging x-ray beam and hence can be used to estimate the attenuation of the beam as the beam passes through an object or the patient 22. During a scan to acquire x-ray projection data, the gantry 12 and the components mounted therein rotate about a center of rotation 24. FIG. 2 shows only a single row of detector elements 20 (i.e., a detector row). However, the multi-slice detector array 18 includes a plurality of parallel detector rows of detector elements 20 such that projection data corresponding to a plurality of quasi-parallel or parallel slices can be acquired simultaneously during a scan.

Rotation of components on the gantry 12 and the operation of the x-ray source 14 are governed by a control mechanism 26 of CT system 10. The control mechanism 26 includes an x-ray controller 28 that provides power and timing signals to the x-ray source 14 and a gantry motor controller 30 that controls the rotational speed and position of components on the gantry 12. A data acquisition system (DAS) 32 in the control mechanism 26 samples analog data from the detector elements 20 and converts the data to digital signals for subsequent processing. An image reconstructor 34 receives sampled and digitized x-ray data from the DAS 32 and performs high-speed image reconstruction. The reconstructed image is applied as an input to a computer 36 that stores the image in a storage device 38. The image reconstructor 34 can be specialized hardware or computer programs executing on the computer 36.

The computer 36 also receives commands and scanning parameters from an operator via a console 40 that has a keyboard and/or other user input and/or marking devices, such as a mouse, trackball, or light pen. An associated display 42, examples of which include a cathode ray tube (CRT) display, liquid crystal display (LCD), or plasma display, allows the operator to observe the reconstructed image and other data from the computer 36. The display 42 may include a user pointing device, such as a pressure-sensitive input screen. The operator supplied commands and parameters are used by the computer 36 to provide control signals and information to the DAS 32, x-ray controller 28, and gantry motor controller 30. In addition, the computer 36 operates a table motor controller 44 that controls a motorized table 46 to position the patient 22 in the gantry 12. For example, the table 46 moves portions of the patient 22 through a gantry opening 48.

In one embodiment, the computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, the computer 36 executes instructions stored in firmware (not shown). The computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiments mentioned above generally describe what is known as a third generation CT system, the methods described herein equally apply to fourth generation CT systems (stationary detector—rotating x-ray source) and fifth generation CT systems (stationary detector and x-ray source), as well as first and second generation CT systems. Additionally, it is contemplated that the benefits of the various embodiments of the invention accrue to imaging modalities other than CT. Further, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

In operation, the CT system 10, including, for example, a spiral CT scanner, may perform a CTA exam that essentially uses x-rays to visualize blood flow in arterial and venous vessels throughout the body of a patient 22, from arteries serving the brain to those bringing blood to the lungs, kidneys, and arms and legs. The beams of x-rays 16 are projected through an area of interest in the patient's body from several different angles to create cross-sectional images that are then assembled by computer into a three-dimensional picture of the area being studied. CTA may be used to, for example, examine the pulmonary arteries in the lungs, visualize blood flow in the renal arteries (those supplying the kidneys), identify aneurysms in the aorta or in other major blood vessels, identify a small aneurysm or arteriovenous malformation inside the brain, identify dissection in the aorta or major branches of the aorta, detect atherosclerotic disease that has narrowed the arteries to the legs, detect thrombosis (clots) in veins, among others.

When performing a CTA exam, a dose of contrast material is typically injected into a vein of the patient 22 to make the blood vessels in the patient 22 stand out when imaged. An automatic injector machine (not shown) may be used and that controls the timing and rate of injection, which may continue during part of the time images are acquired by the CT system 10. During the examination, and for example, a fan-shaped beam of x-rays 16 is projected as the gantry 12 rotates with the detector array 18 detecting the x-ray beams 16 that pass through the patient 22. The acquired scan data is processed and an image reconstructed using any known reconstruction process. The image data then may be stored.

Figure 3:
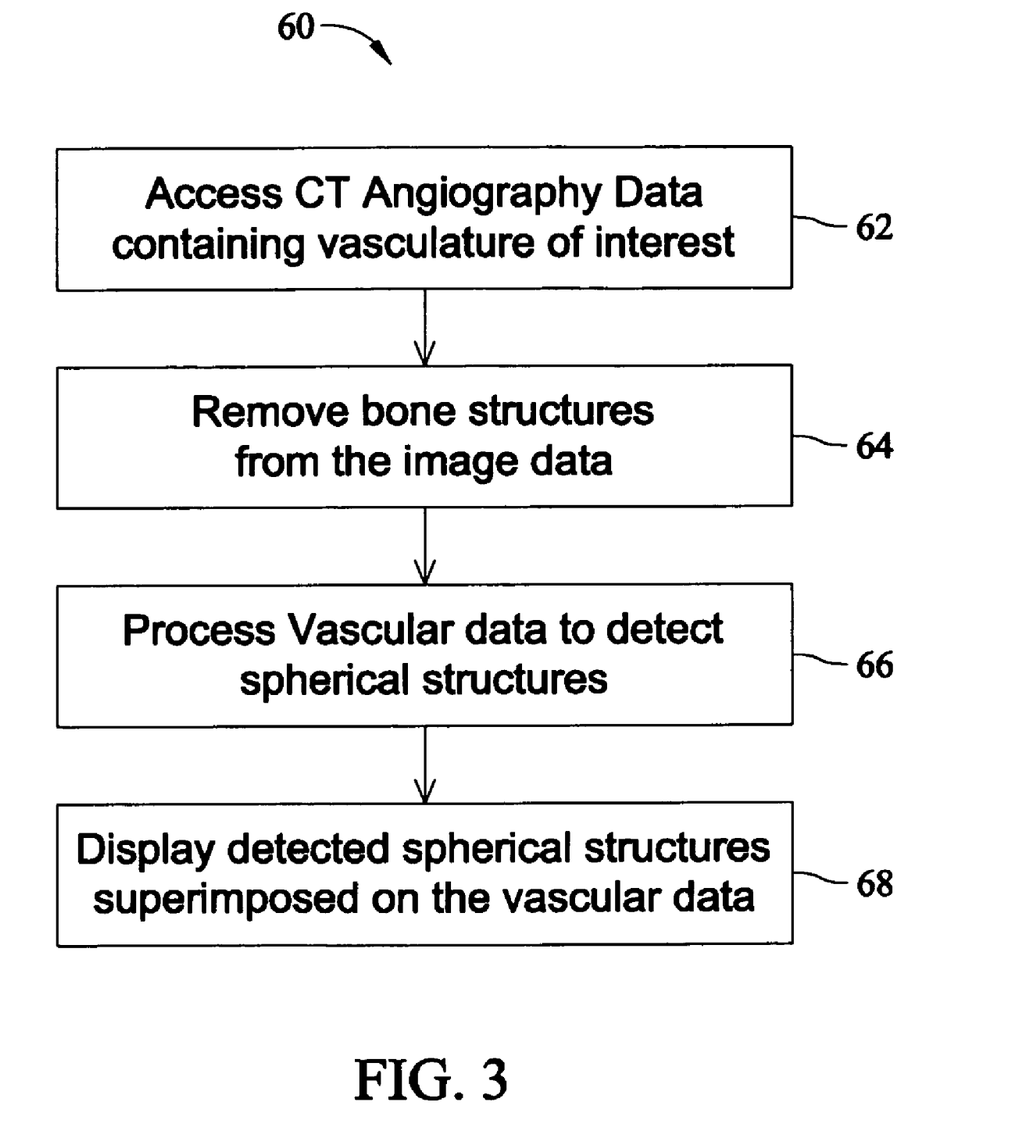
FIG. 3 is a flow chart representative of some embodiments of the present invention showing the processing of CT angiography data to detect aneurysms.

In various embodiments, the stored image data, which may be, for example, three-dimensional (3D) angiography image data that includes a vasculature of interest, for example, in the brain, is processed to detect abnormalities, such as aneurysms. In particular, one method 60 of processing image data is shown in FIG. 3. It should be noted that although the method 60 is described in connection with processing CT angiography data to detect aneurysms, the method 60 is not limited to just this type of processing, but may be used to process different types of image data to detect different types of abnormalities. The method includes at 62 accessing CT angiography data, and in particular, such data that includes vasculatures of interest. For example, the CT angiography data may include vasculatures in the brain of a patient.

Thereafter, at 64, the image data is processed to remove bone structures. It should be noted that when processing is performed by the method 60, this processing may be performed, for example, using the computer 36 of the CT system 10 (both shown in FIG. 2). The bone removal process generally removes obstructing structures in the CT images, such as bones. For example, the computer 36 may be configured to label two or more regions within a volume imaging slice, to flood-fill the interior of each labeled region, and to compute a distance map of each flood-filled region. Thereafter, the computer computes one or more statistics for each region using at least one of the volume imaging slice, the distance map, and the flood-filled region and applies a rule-based classifier to the one or more statistics for each region to classify each region as one of bone, vessel, and indeterminate. Essentially, a bone masking process is performed. However, masking of different types of structures also may be performed.

More particularly, image data such as a reconstructed stack of axial slices that may be formatted in the Digital Imaging and Communications In Medicine (DICOM) standard, is processed. Each slice of the image data may be processed to exclude soft tissue including skin and fat. This soft tissue removal process may be accomplished by employing a simple image threshold and excluding all voxels with image intensities below this soft tissue threshold. For example, a soft tissue removal threshold value of about 176 Hounsfield Units (HU) may be employed in one embodiment to provide a differentiation between most bones and contrast-enhanced vessels. In other embodiments, empirically or statistically derived thresholds may be employed to provide a desired degree of bone and vessel differentiation. After the soft tissue is removed, small islands of tissue may remain which, due to reasons of local anatomy, are associated with intensity values above the soft tissue threshold. Such small islands are typically too small to be regions of bone and may be present due to the presence of very small vessels or due to acquisition or reconstruction noise. The image data is thereafter processed to remove any of these small islands that are present and to produce a noise-reduced image. Removing the small islands also may be accomplished utilizing thresholding, such as by employing a size threshold, such as twenty millimeters squared so that small regions below the size threshold are eliminated from each image slice.

Each region remaining in the noise-reduced image then may be labeled that provides a unique label to all voxels that form, for example, each contiguous region. Each voxel of a region is assigned an intensity value associated with that region such that the labeled region has a uniform intensity.

It should be noted that holes or voids may exist within some of the contiguous regions. The holes may arise due to the differential image intensity generated by, for example, relatively dense cortical bone and the less dense trabecular bone regions. In particular, due to the use of the thresholds, some regions of bone interior may have been incidentally discarded. The holes may prevent the identification, and removal, of the entire bone cross-section within each slice. To identify the entire bone cross-section and not just the cortical bone, the interior of each region in each slice may be completely filled. The labeled image may therefore undergo a constrained flood-fill of the region interiors to produce a flood-filled image. The constrained-fill process assigns the voxels corresponding to the holes the same label and intensity as the surrounding voxels. This may be accomplished by iteratively applying a connectivity process that determines the interior status of each voxel comprising a hole based upon a degree of connectivity with a labeled region. The iterative process proceeds until all holes are filled and labeled to coincide with the surrounding region.

After each region has been filled, a region-specific distance transform may be computed to form a distance-transformed image. In this depicted distance-transformed image, the distance of each voxel in a region from the nearest edge of the region is calculated. Each voxel in each region is assigned an intensity value corresponding to its distance from the nearest edge of its region. In the resulting image, voxel intensity increases the farther the voxel is from the nearest edge of the region. Voxel intensity, therefore, corresponds to the likelihood that the voxel is part of the labeled region. Various model-based statistics then may be computed for each region of each slice using the original image data, the flood-filled image, and the distance-transformed image. One example of a statistic which may be computed is the standard deviation of intensity values for each region, as determined by reference to the original image data and the flood-filled image. The standard deviation then may be used to differentiate vessels from bone in cross-section. In particular, the lumen of a contrast-enhanced vessel may have a substantially uniform intensity relative to bone that may have high intensity on the periphery due to the presence of cortical bone and low intensity on the interior due to the presence of trabecular bone. As a result, lower standard deviations may be associated with vessels while higher standard deviations are indicative of bone.

Other statistics that may be computed for each region include area, mean intensity, the proportion of the region attributable to flood filling, the maximum distance to the periphery, the mean and standard deviation of intensity at a minimum distance in the distance-transformed image (e.g., intensity at the region periphery), the mean and standard deviation of intensity at a maximum distance in the distance-transformed image (e.g., intensity at the region interior), intensity covariance in the interior of the region at various angles, the percentage of pixels within the region with high intensities, such as greater than 376 HU, the maximum intensity at a minimum distance in the distance transformed image, the mean and standard deviation radius of the region, and the local mean and standard deviation of image intensity along the region perimeter, among others. These statistics may be computed to test for such features as texture, leverage, and circularity that in turn also may help distinguish bone from vessels. To the extent that other structure masks may be created, such as a muscle mask, other statistics may be computed, such as statistics related to edge continuity or strength or conformance to an expected shape.

Upon calculation of the various statistics, a sequential rule-based classifier may be applied to the statistical results for each region to classify each region by structure type, such as vascular and bone regions. The sequential rule-based classifier may use various bone or vascular-identification criteria that can be assessed statistically to classify bone and vessel regions respectively. For example, the classification rules may include rules for classifying stented and calcified vessels, rules for identifying vessels, rules for identify bone, and rules for removing small regions labeled as bone which are too small to be bone or which are located where bone is generally not present. In one example, application of the rules to the statistics results in each region being classified as either bone, vessel, or indeterminate.

It should be noted that identification of vessels may be by shape, as determined from the statistics, such as region size, circularity, or other image related statistics. Also, rules for bone identification may look at regions with a high standard deviation or with high mean and minimal standard deviation along the region periphery. Other statistics that may be indicative of bone include minimal standard deviation with a fold, large regions with a large standard deviation, trabecular texture as determined by various measures of covariance, and low standard deviation with a high percentage calcification. After application of the classification rules, each region will be classified structurally, such as bone, vessel or indeterminate, as noted above. The classified regions form a rule-classified image that may be further processed. The rule-based classification may be skewed toward classifying ambiguous regions conservatively to minimize false positives, for example, labeling vessels as bone, which might lead to the accidental exclusion of vascular regions.

Complex regions of the rule-classified image may be analyzed to detect bone-vessel connectedness. Bone-vessel regions that are not connected are included in a labeled output mask. If a bone and a vessel region are determined to be connected, such as by a bridge region, the connected regions are subdivided into two or more regions, such as the unconnected bone region and the vessel region. The process of subdividing may be accomplished by using a de-bridging algorithm. For example, such an algorithm may shrink the labeled regions by eroding the peripheries until the regions are no longer connected. The subdivided regions are then included in the labeled output mask. In the labeled output mask, regions are labeled as either bone, vessel, or mixed, if not separable by de-bridging.

The classification of the labeled regions of the output mask may be further assessed by comparison to the neighboring regions in adjacent or proximate image slices. Respective regions within the two preceding slices or the preceding and subsequent slices may be used to assess the classification of a region, thereby incorporating a third-dimension into the processing. For example, a constrained region-growing process can be performed within the reconstructed slices on regions identified as vascular or circulatory, including organs such as the kidneys, urethra, bladder, etc. in addition to the vessels. The region-growing process may include identifying contiguous regions labeled as vessels within the adjacent or proximate slices to determine the three-dimensional circulatory structure. The region-growing process occurs for each slice of the imaged volume using region-growing seeds from each region labeled as vessel. The region-growing process may be limited by the maximum intensity of the seed pixels and by the range of intensities into which expansion may occur. For example, the region-growing process may be constrained not to connect to regions labeled as bone or to regions that might appear as bone, for example, high-intensity regions.

After the three-dimensional circulatory structure has been determined by the region growing step process, the vessels comprising the region may be dilated by supplementing the peripheral zone around the vessels. Dilation protects voxels in the neighborhood of the vessels from further processing or inclusion in the bone mask, thereby protecting the vessel structure as it has been determined. The vessel dilation accordingly provides a protective buffer to prevent inclusion of vessel voxels into the bone mask in subsequent processing.

A bone construct is subsequently assembled by combining the bone-labeled regions from the output mask with any high intensity regions selected from the original image data and excluding the dilated vessel region, as previously determined. High intensity regions may be selected based upon some intensity threshold, such as 176 HU, and may include bone that has been incidentally discarded in processing. The bone construct is comprised of all regions within the set of image slices that might be bone as determined by labeling and intensity and by excluding those regions determined to be a vessel. The bone-labeled regions of the output mask are then selected and in combination with the bone construct assembled previously, are grown as a three-dimensional bone structure to encompass probable or suspected bone regions. The bone-growing process is performed for each slice of the imaged volume using region-growing seeds from each region labeled as bone. Growth of the three-dimensional bone region may be guided by the results of a three-dimensional connectivity analysis in which the respective bone regions of proximate slices are compared to determine the presence or absence of the three-dimensional bone structure. As with vessel growing, neighboring regions in proximate slices may be used to determine the classification of a region as bone for inclusion in the three-dimensional bone structure.

The seeds for the growing algorithm may be based upon the prior bone classification results. The seeds are the initial points in an image for starting a process. In the various embodiments, the seeds are the points that correspond to high density regions (e.g., 2500 HU or higher). The bone growing process need not be constrained because the known vessel regions are protected due to their exclusion during assembly of the bone construct. Subsequent to the bone growing process, the interior bone regions are flood filled at step to eliminate any remaining holes or gaps in the bone region, resulting in a bone mask. The bone mask may then be excluded from the image data. The remaining image data may then be volume rendered, such as by maximum intensity projection (MIP) or by other known techniques, to produce a bone-free volume rendering. Particular implementations of removing obstructing structures in CT images are described in U.S. Pat. No. 7,123,760, assigned to the assignee of the present invention, and incorporated by reference herein in its entirety.

It should be noted that the removal of bones structures may be performed using different methods. For example, instead of using threshold values to classify structures, other characteristics may be used, such as anatomic properties, etc. In general different processes may be used that provide data visualization enhancements through removal of different structures, such as dominating structures.

Figure 4:
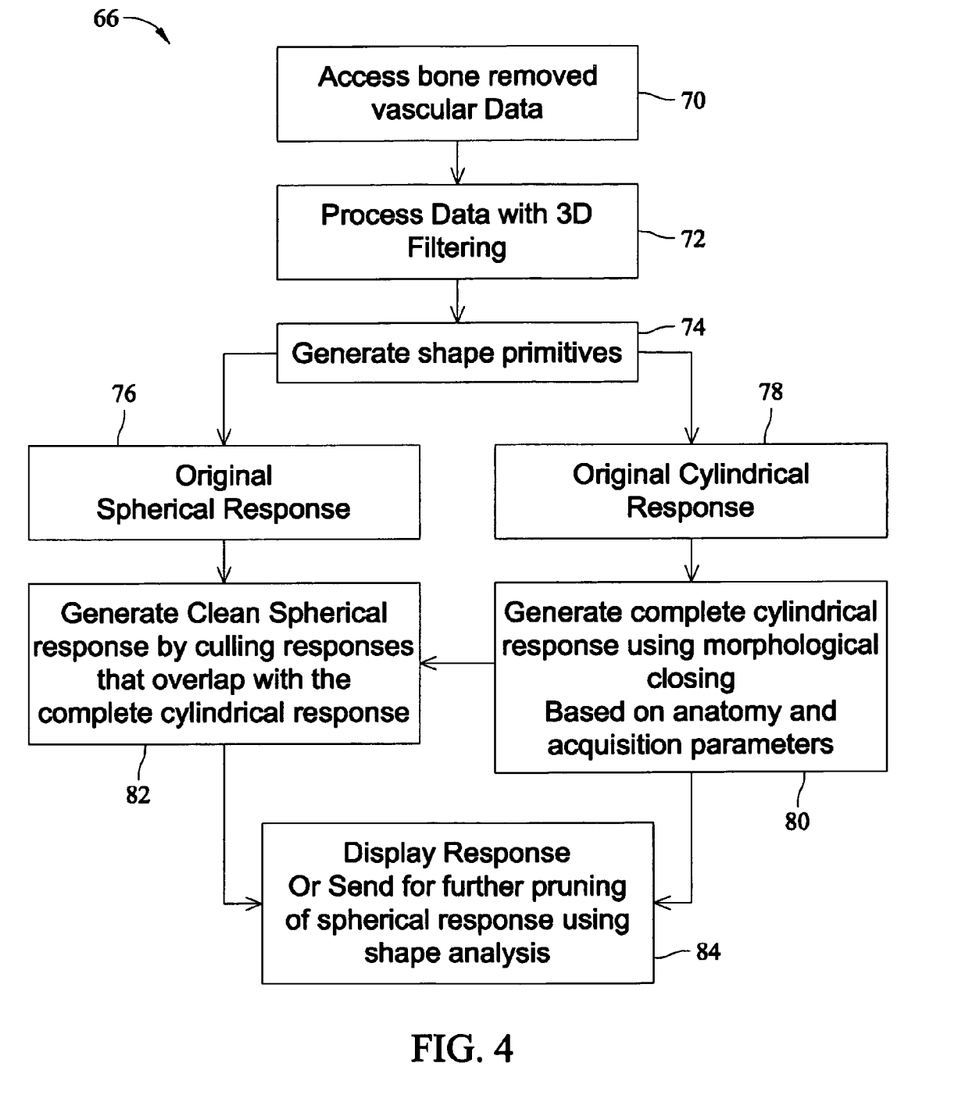
FIG. 4 is a flow chart showing one embodiment of a method of the present invention to identify spherical structures in CT angiography data.

The bone-free volume rendering, for example, 3D CTA image data having bones structures removed is then processed at 66 to detect and extract spherical structures. In particular, a curvature tensor process is performed to determine local curvature values. Essentially, the degree of cylindricalness or sphericalness of an underlying object is determined. In particular, and as shown in FIG. 4, bone removed vascular data is accessed at 70 and 3D filtered at 72 using any known 3D filtering process, with the output of 3D the filtering separated into different response types using shape primitives generated at 74. In particular, the degree of cylindricalness or sphericalness is determined from a resulting original spherical response at 76 and an original cylindrical response at 78. The overlap of the disparate responses is reduced by using a-priori anatomical information. For vascular aneurysm, as an example, the 3D responses are determined with formulation using local curvature at implicit isosurfaces. The curvature tensor determines the local curvatures Kmin and Kmax in the null space of the gradient. The respective curvatures can be determined using the following equation:

$$k_i = (\min\hat{v}, \max\hat{v}) \frac{-\hat{v}^T N^T H N \hat{v}}{\|\nabla I\|} \quad (1)$$

where k is the curvature, v is a vector in the N null space of the gradient of image data I with H being its Hessian. The solution to equation 1 are the eigen values of the following equation:

$$\frac{-N^T H N}{\|\nabla I\|} \quad (2)$$

The responses of the curvature tensor (Kmin and Kmax) are then segregated into spherical and cylindrical responses based on thresholds for Kmin, Kmax and the ratio of Kmin/Kmax derived from the size and aspect ratio of the sphericalness and cylindricalness of interest, for example, an aspect ratio of 2:1, a minimum spherical diameter of one millimeter (mm) and a maximum of 20 mm. It should be noted that a different combination of values result in a different shape response characteristic that would be applicable for a different anatomical object, for example, to identify different shaped structures.

The disparate responses established have overlapping regions that can be termed as false responses. A method of removing the false responses includes adjusting the threshold values to compensate for the differing acquisitions. This involves creating a mapping of the thresholds to all possible acquisitions. In one embodiment, anatomical information is utilized in the form of the scale of the responses on large vessels (cylindrical responses) and the intentional biasing of a response towards spherical versus cylindrical to result in the use of morphological closing of the cylindrical response volume to cull any spherical responses that are in the intersection of the "closed" cylindrical responses and the spherical responses. In particular, a complete cylindrical response using morphological closing based on anatomy and acquisition parameters as described herein is obtained at 80. Thereafter, at 82, a clean spherical response is obtained by culling responses that overlap with the complete cylindrical response. It should be noted that a clean response refers to a response where the false spherical response on a vessel is suppressed by masking out that spherical response using a closed cylindrical volume. Also, closing refers to any known morphological operator that fills holes in a volume. Finally, a display of the response may then be provided at 84.

Particular implementations of extracting anatomical shapes is described in U.S. Patent Application Publication 2006/0079743, assigned to the assignee of the present invention, and incorporated by reference herein in its entirety.

It should be noted that instead of using shape based features to, for example, detect and remove spherical objects to identify aneurysms, other features may be used to identify potential abnormalities. For example, texture features may be identified and corresponding structures or shapes extracted based on the identified texture features.

Referring again to FIG. 3, once the spherical structures are detected and extracted at 66, the spherical structure are displayed at 68 superimposed on the original image of the CT angiography vasculature data having the bone structures.

Figure 5:
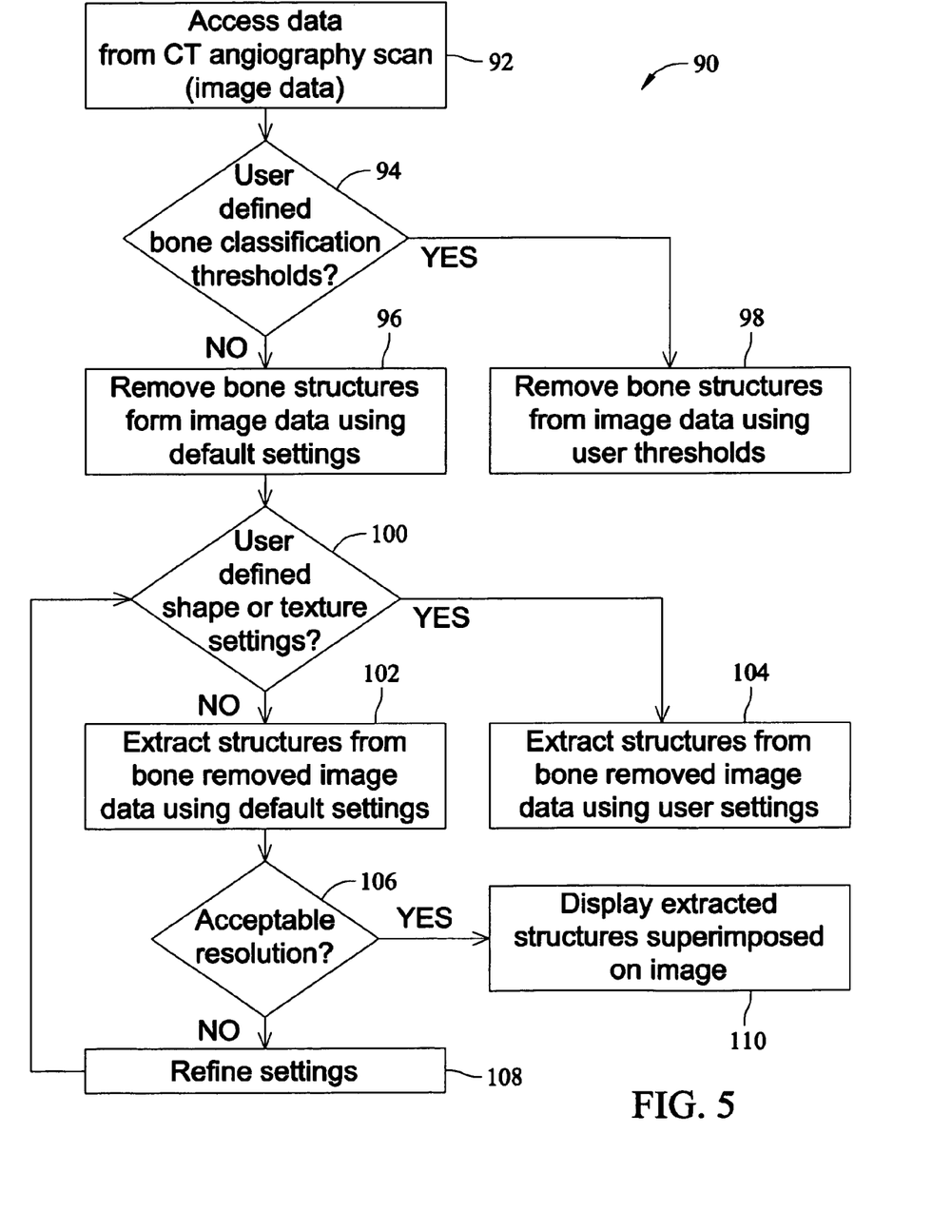
FIG. 5 is a flow chart representative of some embodiments of the present invention showing the processing of CT angiography data to detect abnormalities.

The various embodiments described herein may be used in general to identify potential abnormalities in image data. For example, as shown in FIG. 5, a method 90 for processing image data to identify potential abnormalities includes accessing at 92 data from a CTA scan, for example, 3D image data. Once the image data is accessed, a determination is made at 94 as to whether user defined bone classification thresholds have been inputted or set for a bone removal process. If there are no user defined settings, then at 96, bone structures are removed form the image data using default settings, for example, default HU bone classification settings. If user defined settings are provided, then at 98, bone structures are removed from the image data using the user defined settings. These settings essentially define the bone removal mask settings. Thereafter, at 100 a determination is made as to whether there are any user defined shape or texture settings for an extraction process. If no user settings are provided, then at 102, structures are extracted from the bone removed image data using default settings. If user settings are provided, then at 104, structures are extracted from the bone removed image data using the user settings. The shape settings may include local curvature settings as described above to differentiate between cylindrical and spherical structures. The texture settings may include local gradient changes that identify the texture of potential abnormalities. However, it should be noted that different characteristics, properties, settings, thresholds, etc. may be used during the extraction process.

A determination is then made at 106 as to whether the extracted structures provide an acceptable resolution level, for example, to identify potential abnormalities in a region of interest. This may include a determination of whether the potential abnormalities are clearly identified. If the resolution is not acceptable, the settings are refined at 108, for example, by changing threshold settings, etc. If the resolution is acceptable, then at 110, the extracted structures, for example, spheres are displayed superimposed on image formed from the original image data.

Figure 6:
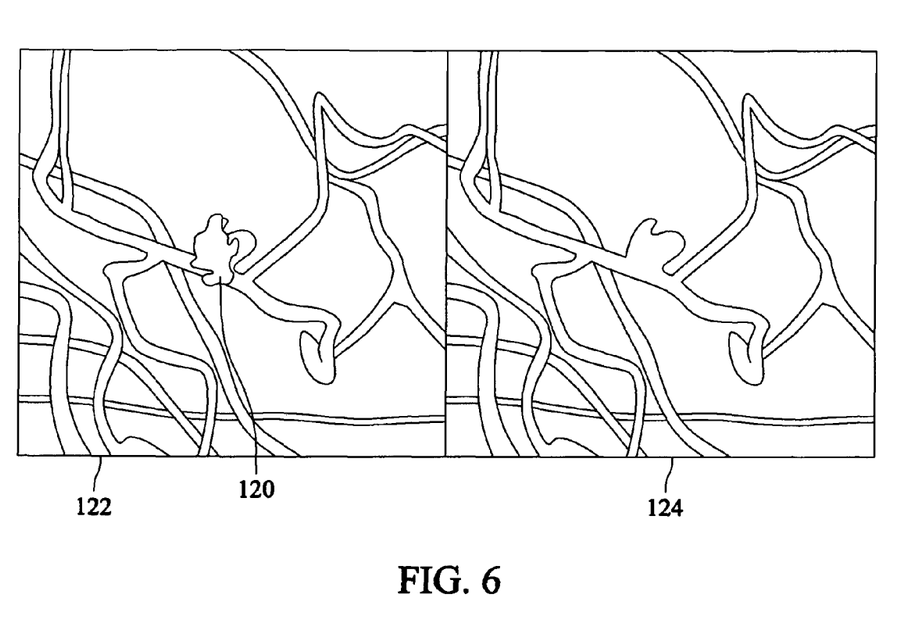
FIG. 6 is a display illustrating a superimposed region on a CT angiography image formed in accordance with various embodiments of the invention.

Thus, as shown in FIG. 6, a detected aneurysm as identified by the superimposed region 120 is displayed on an image 122 of a vasculature of interest. The original image 124 also may be displayed, for example, in a side by side configuration. Also, it should be noted that one or more superimposed regions 120 may be displayed and identified, for example, by a color coded portion. For example, extracted spherical shapes may be color coded for easier detection on an image (e.g., conspicuity).

Thus, various embodiments of the invention provide detection of abnormalities in image data, for example, detection of aneurysms in vasculatures using extracted features, such as shape or texture features. An image with a superimposed display facilitates identification of the potential abnormality.

While the invention has been described in terms of various specific embodiments, those skilled in the art will recognize that the various embodiments of the invention can be practiced with modification within the spirit and scope of the claims.

What is claimed is:

1. A method for detecting aneurysms, said method comprising:
   removing bone structures from three-dimensional (3D) computed tomography (CT) angiography image data;
   identifying texture based features from the bone removed 3D CT angiography image data;
   extracting spherical shapes from the bone removed 3D CT angiography image data based on the identified texture based features to identify aneurysms based on the extracted spherical shapes; and
   displaying the extracted spherical shapes on an image of the 3D CT angiography image data.

2. A method in accordance with claim 1 wherein the displaying comprises superimposing the extracted spherical shapes on the 3D CT angiography image data.

3. A method in accordance with claim 1 further comprising determining the spherical shapes based on a determined local curvature.

4. A method in accordance with claim 3 further comprising differentiating between spherical shapes and cylindrical shapes based on the determined local curvature.

5. A method in accordance with claim 4 wherein the differentiating comprises using response thresholds to identify spherical shapes and cylindrical shapes.

6. A method in accordance with claim 5 wherein the differentiating further comprises using at least one of a size and an aspect ratio of sphericalness and cylindricalness to determine the thresholds.

7. A method in accordance with claim 1 wherein the extracted spherical shapes are color coded.

8. A method in accordance with claim 1 further comprising determining spherical responses and cylindrical responses to identify spherical shapes.

9. A method in accordance with claim 8 further comprising removing spherical responses that overlap with cylindrical responses.

10. A method in accordance with claim 8 further comprising morphologically closing a cylindrical response volume.

11. A method in accordance with claim 10 wherein the morphological closing is based on at least one of anatomy parameters and acquisition parameters.

12. A method for detecting abnormalities, said method comprising:
    removing bone structures from three-dimensional (3D) computed tomography (CT) angiography image data;
    identifying texture based features from the bone removed 3D CT angiography image data;
    extracting structures corresponding to potential vessel abnormalities from the bone removed 3D CT angiography image data based on the identified texture based features; and
    identifying vessel abnormalities based on the extracted structures.

13. A method in accordance with claim 12 wherein the abnormalities comprise aneurysms.

14. A method in accordance with claim 12 wherein the shapes include at least one of spheres and cylinders.

15. A method in accordance with claim 12 wherein the shape based features are extracted from a local curvature of a volumetric region of the bone removed 3D CT angiography image data.

16. A medical imaging apparatus having a radiation source, a detector array, an image processor, a display, and a memory, said medical imaging apparatus controlled by a computer configured to operate the medical imaging apparatus to produce angiographic medical images using the radiation source, the detector array, the image processor, the display, and the memory, and said memory having stored therein instructions configured to instruct the computer to generate an image having extracted shapes displayed thereon, said instructions comprising instructions configured to instruct the computer to:
    remove bone structures from three-dimensional (3D) computed tomography (CT) angiography image data;
    identify texture based features from the bone removed 3D CT angiography image data;
    extract spherical shapes from the bone removed 3D CT angiography image data based on the identified texture based features to identify aneurysms based on the extracted spherical shapes; and
    display the extracted spherical shapes on an image of the 3D CT angiography image data.

17. A medical imaging apparatus in accordance with claim 16 wherein the extracted spherical shapes comprise color coded overlays.

18. A medical imaging apparatus in accordance with claim 16 wherein the instructions further comprise instructions configured to instruct the computer to differentiate between spherical shapes and cylindrical shapes based on a determined local curvature.

19. A medical imaging apparatus in accordance with claim 16 wherein the instructions configured to instruct the computer to extract spherical shapes are based on user defined settings.

20. A non-transitory machine-readable medium or media having instructions recorded thereon configured to instruct a computer to generate an image having extracted shapes displayed thereon, said instructions comprising instructions configured to instruct the computer to:
    remove bone structures from three-dimensional (3D) computed tomography (CT) angiography image data;
    identify texture based features from the bone removed 3D CT angiography image data;
    extract spherical shapes from the bone removed 3D CT angiography image data based on the identified texture based features to identify aneurysms based on the extracted spherical shapes; and
    display the extracted spherical shapes on an image of the 3D CT angiography image data.

21. A method in accordance with claim 1 wherein the 3D CT angiography data comprises 3D CT cranial angiography data.

* * * * *